(12) United States Patent
Türk et al.

(10) Patent No.: US 9,725,554 B2
(45) Date of Patent: Aug. 8, 2017

(54) DENDRITIC POLYUREA FOR SOLUBILIZING ACTIVE SUBSTANCES OF LOW SOLUBILITY

(75) Inventors: Holger Türk, Mannheim (DE); Monika Haberecht, Ludwigshafen (DE); Hiroe Yamada, Saarbrücken (DE); Bernd Bruchmann, Freinsheim (DE); Daniel Schönfelder, Brussels (BE); Michael Ishaque, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/511,700

(22) PCT Filed: Nov. 23, 2010

(86) PCT No.: PCT/EP2010/067978
§ 371 (c)(1),
(2), (4) Date: May 24, 2012

(87) PCT Pub. No.: WO2011/064185
PCT Pub. Date: Jun. 3, 2011

(65) Prior Publication Data
US 2012/0238641 A1    Sep. 20, 2012

(30) Foreign Application Priority Data

Nov. 27, 2009   (EP) .................... 09177370

(51) Int. Cl.
| C08G 18/32 | (2006.01) |
| A01N 25/30 | (2006.01) |
| C08G 18/79 | (2006.01) |
| C08G 18/28 | (2006.01) |
| C08G 18/80 | (2006.01) |
| C08G 18/75 | (2006.01) |
| C08G 18/22 | (2006.01) |
| C08G 18/62 | (2006.01) |

(52) U.S. Cl.
CPC ......... *C08G 18/3234* (2013.01); *A01N 25/30* (2013.01); *C08G 18/222* (2013.01); *C08G 18/283* (2013.01); *C08G 18/284* (2013.01); *C08G 18/62* (2013.01); *C08G 18/755* (2013.01); *C08G 18/791* (2013.01); *C08G 18/792* (2013.01); *C08G 18/8064* (2013.01)

(58) Field of Classification Search
None
See application file for complete search history.

(56) References Cited

U.S. PATENT DOCUMENTS

| 5,362,478 | A | * | 11/1994 | Desai ............... A61K 47/48853 |
| | | | | 424/9.322 |
| 5,866,153 | A | * | 2/1999 | Hasslin et al. ................ 424/408 |
| 2003/0021762 | A1 | * | 1/2003 | Luthra .................... A61L 27/20 |
| | | | | 424/78.32 |
| 2005/0186261 | A1 | * | 8/2005 | Avelar et al. .................. 424/445 |
| 2005/0222360 | A1 | * | 10/2005 | Bruchmann ..................... 528/44 |
| 2008/0306237 | A1 | | 12/2008 | Bruchmann et al. |
| 2009/0041813 | A1 | | 2/2009 | Bouillo et al. |
| 2009/0069186 | A1 | * | 3/2009 | Shirley et al. ................ 504/360 |
| 2009/0099319 | A1 | * | 4/2009 | Stumbe et al. .......... 525/440.01 |
| 2010/0122379 | A1 | * | 5/2010 | Dieckmann ............. A01N 25/12 |
| | | | | 800/295 |
| 2010/0179198 | A1 | | 7/2010 | Mertoglu et al. |

FOREIGN PATENT DOCUMENTS

| DE | 29 10 356 | | 9/1980 | |
| WO | WO 2004/113394 | * | 12/2004 | ............... C08F 2/38 |
| WO | WO 2005/075541 | | 8/2005 | |
| WO | WO 2006/087227 | | 8/2006 | |
| WO | WO 2007/125028 | | 11/2007 | |
| WO | WO 2007/135384 | | 11/2007 | |
| WO | WO2008/132179 | * | 11/2008 | |
| WO | WO 2009/007328 | | 1/2009 | |

OTHER PUBLICATIONS

Smith and Friedrich. J. Am. Chem. Soc., vol. 81 (1), pp. 161-163; publication date 1959.*
International Search Report, PCT/EP2010/067978, Mar. 24, 2011.
International Preliminary Report on Patentability, PCT/EP2010/067978, Jul. 2011.

* cited by examiner

*Primary Examiner* — Johann R Richter
*Assistant Examiner* — Katherine Peebles
(74) *Attorney, Agent, or Firm* — Brinks Gilson & Lione

(57) ABSTRACT

The present invention provides a composition comprising an amphiphile and an active ingredient whose solubility in water at 20° C. is not more than 10 g/L, wherein the amphiphile comprises a dendritic polyurea which is joined to at least one linear or comb-type polymer, and the joining is effected via a difunctional linker, if the repeat units of the linear polymer are composed of polymerized alkylene oxide. The invention also relates to an amphiphile comprising a dendritic polyurea and a process for preparing the amphiphile.

11 Claims, No Drawings

DENDRITIC POLYUREA FOR SOLUBILIZING ACTIVE SUBSTANCES OF LOW SOLUBILITY

This application is a National Stage application of International Application No. PCT/EP2010/067978 filed Nov. 23, 2010, the entire contents of which is hereby incorporated herein by reference. This application also claims priority under 35 U.S.C. § 119 to EP Patent Application No. 09177370.5, filed Nov. 27, 2009, the entire contents of which is hereby incorporated herein by reference.

The present invention provides a composition comprising an amphiphile and an active ingredient whose solubility in water at 20° C. is not more than 10 g/L. The invention also relates to an amphiphile comprising a dendritic polyurea, and a process for preparing the amphiphile. Combinations of preferred features with other preferred features are embraced by the present invention.

Many cases require hydrophobic active ingredients to be solubilized in water without causing any chemical change to the active ingredient in question as such. For this purpose it is possible, for example, to prepare an emulsion, with the active ingredient in question being situated in the oil phase of the emulsion. For many active pharmaceutical ingredients or especially crop protection agents, however, especially those which are to be transported with a body fluid or in the sap of a plant, a procedure of this kind is not possible. Under the action of high shearing forces, emulsions may break. Moreover, sterilizing while maintaining the emulsion is in many cases not possible.

Compositions comprising an active ingredient and an amphiphile based on a polyurea are common knowledge: WO2006/087227 discloses an active ingredient composition comprising a nitrogen-atom-containing hyperbranched polymer and an active ingredient whose solubility in water at 25° C. is not more than 10 g/l. Suitable hyperbranched polymers are polyureas which can be subjected to a polymer-analogous reaction with low-molecular-weight compounds or with polyetherols. The polymer-analogous reaction is in this case effected directly with the hyperbranched polymer. WO 2009/021986 discloses a seed dressing comprising an active ingredient and a hyperbranched polymer, which may be a hyperbranched polyurea, for example. The hyperbranched polymers can either be alkoxylated with alkylene oxides or else reacted directly with polyether alcohols.

Hyperbranched polyureas are common knowledge and preparation processes are described in detail, for example in WO 2003/066702, WO 2005/075541 and WO 2005/044897.

A disadvantage of the known amphiphiles for solubilizing hydrophobic active ingredients in aqueous media is that they are able to solubilize only small amounts of active ingredient. Moreover, the amphiphiles themselves are often not water-soluble or water-dispersible, and so are not suitable for solubilization in aqueous media. A further disadvantage is that the direct alkoxylation of dendritic polyureas does not in practice yield virtually any conversion to the desired product. The reason is that, owing to the restricted solubility of the polyureas, the reaction must be carried out preferably in alcohols, and so ethoxylated solvent (i.e., ethoxylated alcohols) is obtained as a secondary component to a large extent. Other suitable solvents such as dimethylformamide or dimethyl sulfoxide are partly decomposed or degraded by the KOH catalyst under the reaction conditions of the alkoxylation (high temperature, basic pH). If it is possible in spite of this to obtain products by alkoxylation (in the melt, for example), these products, owing to the unequal PEG chain lengths, are often not water-soluble or have relatively poor application properties.

It was an object of the present invention to find an alternative amphiphile suitable for solubilizing sparingly soluble active ingredients in an aqueous medium. A further object was to find an amphiphile which is able to solubilize very high quantities of active ingredient, especially active agrochemical ingredient. Moreover, the amphiphile ought itself to be water-soluble or water-dispersible. A further object, finally, was to find an amphiphile can be prepared from prefabricated components, such as prefabricated polymers.

The object has been achieved by means of a composition comprising an amphiphile and an active ingredient whose solubility in water at 20° C. is not more than 10 g/L, the amphiphile comprising a dendritic polyurea which is joined to at least one linear or comb-type polymer, and the joining being effected via a difunctional linker, if the repeat units of the linear polymer are composed of polymerized alkylene oxide.

The solubility of the active ingredient in water at 20° C. is not more than 10 g/L, preferably not more than 2 g/l, more preferably not more than 0.5 g/l, and especially not more than 0.1 g/l. The composition may comprise one or more different active ingredients. Examples of active ingredients are active agrochemical ingredients, active cosmetic ingredients, active pharmaceutical ingredients or nutritional supplements (such as vitamins and carotenoids). Preferred active ingredients are active agrochemical ingredients.

Examples of active cosmetic ingredients are cosmetic oils, aromas and flavors, vitamins or UV absorbers. Cosmetic oils include peanut oil, jojoba oil, coconut oil, almond oil, olive oil, palm oil, castor oil, soybean oil or wheatgerm oil, or essential oils such as dwarf pine oil, lavender oil, rosemary oil, spruce needle oil, pine needle oil, eucalyptus oil, peppermint oil, sage oil, bergamot oil, turpentine oil, balm oil, juniper oil, lemon oil, anise oil, cardamom oil, camphor oil, etc., or mixtures thereof. UV absorbers include 2-hydroxy-4-methoxybenzophenone, 2,2',4,4'-tetrahydroxybenzophenone, 2,2'-dihydroxy-4,4'-dimethoxybenzophenone, 2,4-dihydroxybenzophenone, 2'-ethylhexyl 2-cyano-3,3-diphenylacrylate, 2,4,6-trianilino-p-(carbo-2'-ethylhexyl-1'-oxy)-1,3,5-triazine, 3-(4-methoxybenzylidene)camphor, 2-ethylhexyl N,N-dimethyl-4-amino-benzoate, 3,3,5-trimethylcyclohexyl salicylate, 4-isopropyldibenzoylmethane, 2-ethylhexyl p-methoxycinnamate, and 2-isoamyl p-methoxycinnamate, and mixtures thereof.

Examples of aromas and flavors are as described in WO 01/49817 or in "Flavors and Fragrances", Ullmann's Encyclopedia of Industrial Chemistry, Wiley-VCH, 2002, hereby incorporated by reference.

Examples of vitamins are vitamins, provitamins and vitamin precursors form the groups A, C, E, and F, more particularly 3,4-didehydroretinol, beta-carotene (provitamin of vitamin A), ascorbic acid (vitamin C), and the palmitic esters, glucosides or phosphates of ascorbic acid, tocopherols, more particularly alpha-tocopherol and its esters, such as the acetate, nicotinate, phosphate, and succinate, for example; and also vitamin F, which is understood to constitute essential fatty acids, particularly linoleic acid, linolenic acid, and arachidonic acid.

Examples of active pharmaceutical ingredients include the following: benzodiazepines, antihypertensives, vitamins, cytostatics—especially taxol, anesthetics, neuroleptics, antidepressants, antivirals, such as anti-HIV agents, antibiotics, antimycotics, antidementia drugs, fungicides, chemotherapeutic agents, urologicals, platelet aggregation inhibitors, sulfonamides, spasmolytics, hormones, immunoglobulins, sera, thyroid therapeutics, psychoactive drugs, anti-Parkinson agents and other anti-hyperkinetics, ophthalmologicals, neuropathy products, calcium metabolism regulators, muscle relaxants, anesthetics, lipid-lowering agents, hepatotherapeutics, coronary agents, cardiac agents, immunotherapeutics, regulatory peptides and their inhibitors, hypnotics, sedatives, gynaecologicals, gout remedies, fibrinolytics, enzyme products and transport proteins, enzyme inhibitors, emetics, blood flow stimulators, diuretics, diagnostic aids, corticoids, cholinergics, biliary therapeutics, antasthmatics, bronchodilators, beta-receptor blockers, calcium antagonists, ACE inhibitors, arteriosclerosis remedies, antiinflammatories, anticoagulants, antihypotensives, antihypoglycemics, antihypertensives, antifibrinolytics, antiepileptics, antiemetics, antidotes, antidiabetics, antiarrythmics, antianemics, antiallergics, antelmintics, analgesics, analeptics, aldosterone antagonists, slimming agents.

The term "active agrochemical ingredients" (also called pesticides below) refers to at least one active ingredient selected from the group of fungicides, insecticides, nematicides, herbicides, safeners and/or growth regulators. Preferred pesticides are fungicides, insecticides and herbicides, especially insecticides. Mixtures of pesticides from two or more of the aforementioned classes can also be used. The skilled person is familiar with such pesticides, which can be found in Pesticide Manual, 14th Ed. (2006), The British Crop Protection Council, London, for example. Suitable insecticides are insecticides from the class of the carbamates, organophosphates, organochlorine insecticides, phenylpyrazoles, pyrethroids, neonicotinoids, spinosins, avermectins, milbemycins, juvenile hormone analogues, alkyl halides, organotin compounds, nereistoxin analogues, benzoylureas, diacylhydrazines, METI acaricides, and also insecticides such as chloropicrin, pymetrozine, flonicamid, clofentezine, hexythiazox, etoxazole, diafenthiuron, propargite, tetradifon, chlorfenapyr, DNOC, buprofezine, cyromazine, amitraz, hydramethylnon, acequinocyl, fluacrypyrim, rotenone or derivatives thereof. Suitable fungicides are fungicides from the classes of the dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzylcarbamates, carbamates, carboxamides, chloronitriles, cyanoacetamide oximes, cyanoimidazoles, cyclopropanecarboxamides, dicarboximides, dihydrodioxazines, dinitrophenylcrotonates, dithiocarbamates, dithiolanes, ethylphosphonates, ethylaminothiazole carboxamides, guanidines, hydroxyl(2-amino)pyrimidines, hydroxyanilides, imidazoles, imidazolinones, inorganics, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinone hydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, triazoles. Suitable herbicides are herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ethers, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

In one embodiment the pesticide comprises an insecticide, and preferably the pesticide is composed of at least one insecticide. Preferred insecticides are fipronil, allethrin, alpha-cypermethrin, beta-cyfluthrin, bifenthrin, bioallethrin, 4-chloro-2-(2-chloro-2-methylpropyl)-5-[(6-iodo-3-pyridinyl)methoxy]-3(2H)-pyridazinone (CAS RN: 120955-77-3), chlorfenapyr, chlorpyrifos, cyfluthrin, cyhalothrin, cypermethrin, deltamethrin, etofenprox, fenoxycarb, flufenoxuron, hydramethylnon, metaflumizone, permethrin, pyriproxifen, silafluofen, tebufenocide, and tralomethrin. Particularly preferred insecticides are fipronil, alpha-cypermethrin, bifenthrin, chlorfenapyr, cyfluthrin, cypermethrin, deltamethrin, etofenprox, hydramethylnon, metaflumizone, permethrin. Especially preferred insecticides are fipronil, alpha-cypermethrin, deltamethrin, chlorfe-napyr, hydramethylnon, and metaflumizone. An especially preferred insecticide is fipronil. In another embodiment the pesticide comprises a fungicide, and preferably the pesticide is composed of at least one fungicide. Preferred fungicides are pyraclostrobin, metconazole, and epoxiconazole. In another embodiment the pesticide comprises a herbicide, and preferably the pesticide is composed of at least one herbicide. In another embodiment the pesticide comprises a growth regulator, and preferably the pesticide is composed of at least one growth regulator.

The composition of the invention comprises typically 0.1% to 70% by weight of active ingredient, preferably 1% to 50% by weight, more particularly 3% to 30% by weight, based on the composition.

Amphiphiles typically comprise at least one polar (hydrophilic) moiety and at least one apolar (hydrophobic) moiety. Typical amphiphiles are fatty acids, surfactants, and phospholipids. The composition may comprise one or more different amphiphiles.

The composition of the invention usually comprises 0.01% to 40%, preferably 0.05% to 30%, more preferably from 0.1% to 20% by weight of amphiphile. The amphiphile is usually soluble or dispersible in water, i.e., it is possible to prepare a clear (i.e., devoid of particles visible to the naked eye) aqueous solution or dispersion.

In the context of the present invention, the term "dendritic" polymers encompasses, very generally, polymers distinguished by a branched structure and a high functionality. The "dendritic polymers" in the sense of the invention include dendrimers, hyperbranched polymers, and structures derived therefrom.

"Dendrimers" are molecularly uniform macromolecules having a highly symmetric structure. Dendrimers derive structurally from star polymers, with star branching in turn of each of the individual chains. They come about starting from small molecules, by means of a continually repeating reaction sequence, resulting in ever higher numbers of branches, at whose ends there are in each case functional groups which, in turn, are a starting point for further branches. Hence the number of monomer end groups increases with each reaction step, ultimately resulting in a spherical tree structure. A characteristic feature of the dendrimers is the number of reaction stages (generations) carried out for the purpose of their synthesis. On the basis of their uniform structure, dendrimers generally have a defined molar mass.

Of preferential suitability are both molecularly and structurally nonuniform hyperbranched polymers which have side chains with different lengths and different branching, and also a molar mass distribution. Regarding the general definition of hyperbranched polymers, reference is also made to P. J. Flory, J. Am. Chem. Soc. 1952, 74, 2718 and H. Frey et al., Chem. Eur. J. 2000, 6, no. 14, 2499.

Suitability for the synthesis of these hyperbranched polymers is possessed in particular by what are called $AB_x$ monomers. These monomers have two different functional groups, A and B, which are able to react with one another to form a join. The functional group A is present only once per molecule, and the functional group B twice or more. The reaction of said $AB_x$ monomers with one another produces substantially non-crosslinked polymers having regularly arranged branching sites. The polymers have almost exclusively B groups at the chain ends. Further details can be found in, for example, Journal of Molecular Science, Rev. Macromol. Chem. Phys., C37(3), 555-579 (1997).

The hyperbranched polymers used in accordance with the invention preferably have a degree of branching (DB) per molecule of 10% to 100%, more preferably 10% to 90%, and more particularly 10% to 80%. On the definition of the degree of branching, refer to H. Frey et al., Acta Polym. 1997, 48, 30.

Hyperbranched polymers, i.e., polymers with molecular and structural nonuniformity, are used with preference. They are generally easier and hence more economic to prepare than are dendrimers.

The present invention concerns a specific type of dendritic polymers, namely dendrimeric polyureas, more particularly hyperbranched polyureas. The term "polyurea" in the sense of the present invention encompasses polymers which in addition to urea groups may also have urethane groups, allophanate groups, biuret groups, and further functional groups, such as amine functions, for example. The urethane groups are usually O-alkyl urethane groups, the alkyl radical having one to 18 carbon atoms. Preference is given to the O-alkyl urethane groups obtainable by reacting an isocyanate group with a monoalcohol which has been used as blocking agent.

Preference is given to dendritic polyureas which have a weight-average molecular weight in the range from about 500 to 100 000 g/mol, preferably 1000 to 50 000 g/mol. This determination is made usually by gel permeation chromatography using a refractometer as detector. Determination is carried out preferably as described in the examples.

The dendritic polyurea is preferably not soluble or dispersible in water, which means that it is not possible to prepare an aqueous solution or dispersion which is clear (i.e., without particles visible to the naked eye).

Dendritic polyureas, especially hyperbranched polyureas, are, as is known to the skilled worker, available in a variety of ways, as for example by direct reaction of urea with polyamines or by reaction of dialkyl carbonates with polyamines. Polyureas of this invention, however, are obtainable preferably by reaction of a blocked polyisocyanate with polyamines. Other preparation processes have been described; for example, WO 05044897 A1 describes the synthesis of hyperbranched polyureas from carbonates (e.g., diethyl carbonate; A2 monomer) and polyfunctional amines (e.g., triamines; B3 monomers), or WO 05075541 describes the synthesis of hyperbranched polyureas from urea or from urea derivatives (A2 monomers) and polyfunctional amines (e.g., triamines; B3 monomers).

The dendritic polyurea, more particularly the hyperbranched polyurea, is obtainable preferably by a process encompassing the reaction of an at least difunctional blocked di- or polyisocyanate with at least one at least difunctional primary and/or secondary amine, with elimination of the blocking agent, to give the polyurea.

The at least difunctional blocked di- or polyisocyanates may be prepared, for example, from the reaction of di- or polyisocyanates with aliphatic, araliphatic or aromatic alcohols, preferably monoalcohols. Furthermore, they may be prepared, for example, by reaction of primary amines with alcohol and urea in accordance with EP-A-18586, by reaction of primary amines with O-alkyl carbamates in accordance with EP 18588 or EP-A-28338, by reaction of primary amines with dimethyl carbonate in accordance with EP-A-570071, or else by reaction of formamides with dimethyl carbonate or of primary amines with methyl formate in accordance with EP-A-609786. In general it is also possible to use di- or polyisocyanates which are obtained as starting products or intermediates in the synthesis of di- or polyisocyanates prepared without phosgene, in accordance with specifications EP 355443, EP 566925, EP 568782 or DE 19820114.

In the reaction of the di- or polyisocyanates with the di- or polyamines to give the hyperbranched polyureas, the reversibility of the reaction between isocyanate and alcohol in contrast to the irreversibility of the reaction between isocyanate and amine under the prevailing reaction conditions is exploited in order to direct a controlled molecular construction. The alcohol is utilized here in principle as a blocking agent for the isocyanate group, in other words as a moderator for the extreme reactivity of the isocyanate with the amine.

Suitable blocking agents include monoalcohols or blocking reagents, preferably monoalcohols. Suitable monoalcohols are preferably linear or branched aliphatic monoalcohols, such as methanol, ethanol, propanol, butanol, pentanol, hexanol, heptanol, octanol, isopropanol, isobutanol or 2-ethyl-1-hexanol, or araliphatic monoalcohols, such as benzyl alcohol or phenylethanol. Particularly preferred are the linear or branched aliphatic monoalcohols and also benzyl alcohol. Especially preferred are linear aliphatic monoalcohols having 1 to 18, preferably 1 to 6, carbon atoms.

Another embodiment starts from at least difunctional blocked di- or polyisocyanates whose NCO groups have been blocked with what are known as blocking reagents, as described in the prior art. A feature of these blocking reagents is that they ensure a thermally reversible blocking of the isocyanate groups at temperatures in general below 160° C. Blocking agents of this kind are therefore used to modify isocyanate groups which are employed in thermally curable one-component polyurethane systems. Preferred blocking reagents used are phenols, caprolactam, 1H-imidazole, 2-methyl-imidazole, 1,2,4-triazole, 3,5-dimethylpyrazole, malonic acid dialkyl esters, acetanilide, acetone oxime or butanone oxime. Here as well, the reaction with the diamine or polyamine to give the hyperbranched polyurea takes place with elimination of the blocking agent. In the text below, therefore, the NCO groups blocked with monoalcohols or blocking reagents are referred to as "capped NCO groups".

After the reaction, i.e., without modification, the dendritic polyurea, more particularly the hyperbranched polyurea, is terminated either with amino groups or with capped NCO groups. They dissolve readily in polar solvents, such as in alcohols, such as methanol, ethanol, butanol, alcohol/water mixtures, esters such as ethyl acetate and butyl acetate, and also in dimethylformamide, dimethylacetamide, N-methylpyrrolidone, ethylene carbonate or propylene carbonate.

By a dendritic polyurea, more particularly a hyperbranched polyurea, is meant, in the context of this invention, a product which has urea groups and also at least three, preferably at least six, more preferably at least eight functional groups. There is in principle no upper limit on the number of functional groups, although products with a very large number of functional groups may exhibit unwanted properties, such as high viscosity or poor solubility, for example. The high-functionality polyureas of the present invention usually have not more than 100 functional groups, preferably not more than 50 functional groups.

The at least difunctional primary and/or secondary amines used in preparing the dendritic, more particularly hyperbranched, polyureas are selected from compounds which carry at least two amine groups that are reactive with urethane groups.

Compounds having at least two amine groups that are reactive with urethane groups are, for example, ethylenediamine, N-alkylethylenediamine, propylenediamine, 2,2-dimethyl-1,3-propanediamine, N-alkylpropylenediamine, butylenediamine, N-alkylbutylenediamine, hexamethylenediamine, N-alkylhexamethylenediamine, tolylenediamine, diaminodiphenylmethane, diaminodicyclohexylmethane, phenylenediamine, cyclohexyldiamine, diaminodiphenyl sulfone, isophoronediamine, 2-butyl-2-ethyl-1,5-pentamethylenediamine, 2,2,4- or 2,4,4-trimethyl-1,6-hexa-methylenediamine, 2-aminopropylcyclohexylamine, 3(4)-aminomethyl-1-methyl-cyclohexylamine, 1,4-diamino-4-methylpentane, amine-terminated polyoxyalkylene polyols (known as Jeffamines), aminated polytetramethylene glycols, N-amino-alkylpiperidines, ammonia, bis(aminoethyl) amine, bis(aminopropyl)amine, bis(aminobutyl)amine, bis (aminopentyl)amine, bis(aminohexyl)amine, tris(aminoethyl)amine, tris(aminopropyl)amine, tris(aminohexyl) amine, trisaminohexane, 4-aminomethyl-1,8-octamethylenediamine, N'-(3-aminopropyl)-N,N-dimethyl-1,3-propanediamine, trisaminononane or melamine. It is also possible as well to use any desired mixtures of at least two of the stated compounds. Preferred at least difunctional primary and/or secondary amines are at least difunctional primary amines, more preferably difunctional aliphatic primary amines, more particularly isophoronediamine.

Diisocyanates or polyisocyanates contemplated are the aliphatic, cycloaliphatic, araliphatic, and aromatic diisocyanates or polyisocyanates that are known from the prior art and are exemplified below. They include, preferably, 4,4'-diphenylmethane diisocyanate, the mixtures of monomeric diphenylmethane diisocyanates and oligomeric diphenylmethane diisocyanates (polymeric MDI), tetramethylene diisocyanate, tetramethylene diisocyanate trimers, hexamethylene diisocyanate, hexamethylene diisocyanate trimers, isophorone diisocyanate trimer, 4,4'-methylene-bis(cyclohexyl)diisocyanate, xylylene diisocyanate, tetramethylxylylene diisocyanate, dodecyl diisocyanate, lysine alkyl ester diisocyanate, where alkyl stands for C1 to C10, 1,4-diisocyanatocyclohexane or 4-isocyanatomethyl-1,8-octamethylene diisocyanate.

Suitable with particular preference for constructing the polyureas are diisocyanates or polyisocyanates which have NCO groups with different reactivities. Mention may be made here of 2,4-tolylene diisocyanate (2,4-TDI), 2,4'-diphenylmethane diisocyanate (2,4'-MDI), triisocyanatotoluene, isophorone diisocyanate (IPDI), 2-butyl-2-ethylpentamethylene diisocyanate, 2,2,4- or 2,4,4-trimethyl-1,6-hexamethylene diisocyanate, 2-isocyantopropylcyclohexyl isocyanate, 3(4)-isocyanatomethyl-1-methyl-cyclohexyl isocyanate, 1,4-diisocyanato-4-methylpentane, 2,4'-methylene-bis(cyclohexyl) diisocyanate, and 4-methylcyclohexane 1,3-diisocyanate (HTDI). Also suitable for constructing the polyureas are isocyanates whose NCO groups have the same reactivity to start with but in which, through initial addition of a reactant to an NCO group, it is possible to induce a drop in reactivity for the second NCO group. Examples thereof are isocyanates whose NCO groups are coupled via a delocalized electron system, as for example 1,3- and 1,4-phenylene diisocyanate, 1,5-naphthylene diisocyanate, diphenyl diisocyanate, tolidine diisocyanate or 2,6-tolylene diisocyanate.

Additionally it is possible to make use, for example, of oligoisocyanates or polyisocyanates which can be prepared from the aforementioned diisocyanates or polyisocyanates, or mixtures thereof, by joining by means of urethane, allophanate, urea, biuret, uretdione, amide, isocyanurate, carbodiimide, uretonimine, oxadiazinetrione or iminooxadiazinedione structures.

Especially preferred diisocyanates or polyisocyanates suitable for constructing the polyureas are oligoisocyanates or polyisocyanates which can be prepared from aliphatic, cycloaliphatic, araliphatic, and aromatic, preferably aliphatic, diisocyanates or polyisocyanates by joining by means of urethane, allophanate, urea, biuret, uretdione, amide, isocyanurate, carbodiimide, uretonimine, oxadiazinetrione or iminooxadiazine-dione structures, preferably by means of isocyanurate structures. Typically these oligoisocyanates or polyisocyanates have an average NCO functionality of 2.1 to 4.9, preferably 2.9 to 4.4, especially of 3.4 to 3.9. The average molar mass is usually 300 to 3000 g/mol, preferably 400 to 1500 g/mol, more particularly 500 to 800 g/mol.

In the preparation of the high-functionality polyureas it is necessary to set the molar ratio of compounds having at least two amine groups that are reactive with capped NCO groups to the capped isocyanate such that the resulting most simply conceivable condensation product (referred to below as condensation product (A)) comprises on average either one capped NCO group and more than one group that is reactive with the capped NCO group, or one group that is reactive with capped NCO groups and more than one capped NCO group. The simplest structure of the condensation product (A) formed from a capped di- or polyisocyanate (X) and a di- or polyamine (Y) produces the arrangement $XY_n$ or $X_nY$, where n in general represents a number between 1 and 6, preferably between 1 and 4, more preferably between 1 and 3. The reactive group which results as an individual group in this case is referred to below generally as "focal group".

Where, for example, in the preparation of the simplest condensation product (A) from a capped diisocyanate and a divalent amine, the reaction ratio is 1:1, then the result is a molecule of type XY. In the case of the preparation of the condensation product (A) from a capped diisocyanate and a trivalent amine, with a molar reaction ratio of 1:1, the result is a molecule of type $XY_2$. The focal group here is a capped isocyanate group. In the case of the preparation of the condensation product (A) from a capped diisocyanate and a tetravalent amine, again with the reaction ratio of 1:1, the result is a molecule of type $XY_3$. The focal group here is a capped isocyanate group. The condensation product (A) may additionally be prepared, for example, from a capped diisocyanate and a trivalent component which is reactive with the capped diisocyanate, with the reaction ratio being 2:1 on a molar basis. Here the result is a molecule of type $X_2Y$, the focal group here being an amine. Where difunctional compounds, examples being those with two capped isocyanate groups or with two amine groups, are additionally added to the components, the result is an extension of the chains. The result again is a molecule of type $X_2Y$, the focal group being a capped isocyanate.

The reaction product (A) is preferably not isolated. Preferably, in the further course of the process, there is a direct reaction of the reaction products (A) to the hyperbranched polyurea (P).

The reaction to give the condensation product (A) and to give the polycondensation product (P) takes place customarily at a temperature of 0 to 250° C., preferably at 60 to 160° C., in bulk or in solution. In these reactions it is possible generally to use any solvents which are inert toward the respective reactants. Preference is given to using organic solvents, such as, for example, decane, dodecane, benzene, toluene, chlorobenzene, xylene, dimethylformamide, dimethylacetamide or solvent naphtha. In one preferred embodiment the condensation reaction is carried out in bulk. The capping agent released in the course of the reaction with the amine, such as the alcohol used for the urethanization, for example, may be removed from the reaction equilibrium by distillation, optionally under reduced pressure, in order to accelerate the reaction.

In another preferred embodiment, the alcohol used for blocking is employed as a solvent for the reaction. In this case the urethane component is introduced as a solution in the alcohol, and the amine component is added in the appropriate proportion. When the temperature is raised, the alcohol bound in the form of urethane is displaced by the amine component, and the urea of the invention is formed. The alcohol component present in excess also functions as a solvent for the ureas that are formed.

In order to accelerate the reaction it is also possible to add catalysts or catalyst mixtures. Suitable catalysts are generally compounds which catalyze urethane reactions, examples being amines, ammonium compounds, organoaluminum, -tin, -zinc, -titanium, -zirconium or -bismuth compounds. By way of example it is possible to use diazabicyclooctane (DABCO), diazabicyclononene (DBN), diazabicycloundecene (DBU), imidazoles, such as imidazole, 1-methylimidazole, 2-methylimidazole, 1,2-dimethylimidazole, titanium tetrabutoxide, dibutyltin oxide, dibutyltin dilaurate, tin dioctoate, zirconium acetylacetonate or mixtures thereof. The catalyst is added generally in an amount of 50 to 10 000, preferably of 100 to 5000 ppm by weight, based on the amount of isocyanate employed. It is possible, furthermore, to control the intermolecular polycondensation reaction both by adding a suitable catalyst and by selecting a suitable temperature. Moreover, the average molecular weight of the polymer (P) can be adjusted via the composition of the starting components and via the residence time. The condensation products (A) and the polycondensation products (P) which have been prepared at elevated temperature are typically stable for a relatively long period of time at room temperature.

In view of the nature of the condensation products (A) it is possible that the condensation reaction may result in polycondensation products (P) having different structures, with branches but no crosslinks. Furthermore, the polycondensation products (P) contain either a capped isocyanate focal group and more than two groups which are reactive with capped isocyanate groups, or else a focal group which is reactive with capped isocyanate and more than two capped isocyanate groups. The number of reactive groups depends on the nature of the condensation products (A) employed and on the degree of polycondensation.

To terminate the intermolecular polycondensation reaction there are a variety of possibilities. By way of example the temperature can be lowered to a range in which the reaction comes to a standstill and the product (A) or the polycondensation product (P) is stable on storage. In a preferred embodiment, as soon as the intermolecular reaction of the condensation product (A) gives a polycondensation product (P) having the desired degree of polycondensation, the reaction is arrested by adding to the product (P) a product having groups that are reactive toward the focal group of (P). For instance, in the case of a capped NCO focal group, a mono-, di- or polyamine, for example, can be added. In the case of an amine focal group, the product (P) can have added to it, for example, a mono-, di- or polyurethane, a mono-, di- or polyisocyanate, an aldehyde, ketone, or an acid derivative which is reactive with amine.

The dendritic polyureas are prepared generally in a pressure range from 2 mbar to 20 bar, preferably under atmospheric pressure, in reactors or reactor cascades which are operated batchwise, semibatchwise or continuously. Through the aforementioned setting of the reaction conditions and, optionally, through the choice of the suitable solvent, the products of the invention can be processed further without further purification after their preparation.

The amphiphile preferably comprises a dendritic polyurea which is joined to at least one linear or comb-type polymer, and the joining is effected via a difunctional linker, if the repeat units of the linear polymer are composed of a polymerized alkylene oxide.

The molar ratio of dendritic polyurea to the sum of linear and comb-type polymer is usually in the range from 1:1 to 1:100, preferably 1:1 to 1:50, more preferably 1:1 to 1:25.

The linear polymer is preferably
a) a homopolymer or random copolymer comprising a polar ethylenically unsaturated monomer,
b) a block polymer comprising a block of polyethylene glycol or based on at least one polar ethylenically unsaturated monomer, or
c) a polycondensate comprising polyethylene glycol, or
d) a polyethylene glycol,
the polyethylene glycol d) being joined to the dendritic polyurea via a difunctional linker. The linear polymer is more preferably one of the aforementioned polymers a), b) or c). In a further particularly preferred embodiment, the linear polymer is one of the aforementioned polymers a), c) or d). The linear polymer is especially preferably one of the aforementioned polymers a) or c), especially a).

In one embodiment, the linear polymer may be a homopolymer or random copolymer comprising a polar ethylenically unsaturated monomer. The number-average molar mass $M_n$ is usually less than 100 000 g/mol, preferably less than 50 000 g/mol, more preferably less than 20 000 g/mol and most preferably less than 10 000 g/mol, and can be determined by means of GPC and a suitable standard. $M_n$ is typically more than 200 g/mol, preferably more than 500 g/mol.

Suitable polar ethylenically unsaturated monomers are monomers which bear charge or bear ionizable groups and comprise a polymerizable ethylenically unsaturated bond. Examples of charge-bearing or ionizable groups are carboxylic acid, sulfonic acid, polyethylene glycol, alcohol, nitrile, amide, amine, dialkylamine. Examples of polar ethylenically unsaturated monomers are vinylpyrrolidone, (meth) acrylic acid, a sulfo-containing (meth)acrylate (such as 2-acrylamido-2-methylpropanesulfonic acid), an aminofunctional (meth)acrylate (such as dimethylaminoethyl (meth)acrylate), (meth)acrylic esters of a polyethylene glycol derivative (such as polyethylene glycol monomethyl ether (meth)acrylate), itaconic acid, maleic anhydride, $C_1$-$C_{20}$-alkyl (meth)acrylates substituted by OH groups (such as hydroxyethyl (meth)acrylate, hydroxybutyl (meth) acrylate), (meth)acrylonitrile, (meth)acrylamide, N-methylol (meth)acrylamide. Preferred polar ethylenically unsaturated monomers are vinylpyrrolidone, (meth)acrylic acid, polyethylene glycol monomethyl ether (meth)acrylate, polyethylene glycol (meth)acrylate. The expression "(meth) acrylic" means "acrylic" or "methacrylic".

Examples of linear homopolymers comprising a polar ethylenically unsaturated monomer are homopolymers of the aforementioned polar ethylenically unsaturated monomers, preferably of vinylpyrrolidone, (meth)acrylic acid, polyethylene glycol monomethyl ether (meth)acrylate, polyethylene glycol (meth)acrylate.

Examples of random copolymers comprising a polar ethylenically unsaturated monomer are copolymers of the aforementioned polar ethylenically unsaturated monomers, preferably of vinylpyrrolidone, (meth)acrylic acid, polyethylene glycol monomethyl ether (meth)acrylate, polyethylene glycol (meth)acrylate. As further monomer, the random copolymer may comprise: esters of acrylic acid with $C_1$-$C_{10}$-alkanols such as ethyl acrylate, n-butyl acrylate, isobutyl acrylate, tert-butyl acrylate, n-hexyl acrylate, 2-ethylhexyl acrylate and 3-propylheptyl acrylate, the esters of methacrylic acid with $C_1$-$C_{10}$-alkanols such as methyl methacrylate, ethyl methacrylate, n-butyl methacrylate, isobutyl methacrylate, tert-butyl methacrylate and n-hexyl methacrylate, N—($C_2$-$C_{10}$-alkyl)amides of acrylic acid and of methacrylic acid, and the N—($C_1$-$C_2$-alkyl)-N—($C_2$-$C_{10}$-alkyl) amides of acrylic acid and of methacrylic acid, e.g. N-ethylacrylamide, N,N-diethylacrylamide, N-butylacrylamide, N-methyl-N-propyl-acrylamide, N-(n-hexyl)acrylamide, N-(n-octyl)acrylamide and the corresponding methacrylamides, vinylaromatic monomers such as styrene, methylstyrene, vinyltoluene, olefins having 2 to 10 carbon atoms, preferably α-olefins having 3 to 10 carbon atoms, such as propene, 1-butene, 1-pentene, 1-hexene, 1-octene and 1-decene, vinyl esters of aliphatic carboxylic acids such as vinyl acetate, vinyl propionate, vinyl laurate, vinyl nonanoate, vinyl decanoate, vinyl laurate and vinyl stearate, unsaturated nitriles such as acrylonitrile and methacrylonitrile, halogenated olefins such as vinyl chloride, $C_{11}$-$C_{20}$-alkyl esters of monoethylenically unsaturated monocarboxylic acids having preferably 3 to 6 carbon atoms, e.g. $C_{11}$-$C_{20}$-alkyl acrylates and $C_{11}$-$C_{20}$-alkyl methacrylates such as lauryl acrylate, lauryl methacrylate, isotridecyl acrylate, isotridecyl methacrylate, stearyl acrylate, stearyl methacrylate, di-$C_1$-$C_{20}$-alkyl esters of ethylenically unsaturated dicarboxylic acids having preferably 4 to 8 carbon atoms, e.g. di-$C_1$-$C_{20}$-alkyl esters of fumaric acid and of maleic acid such as dimethyl fumarate, dimethyl maleate, dibutyl fumarate and dibutyl maleate, glycidyl esters of monoethylenically unsaturated monocarboxylic acids having preferably 3 to 6 carbon atoms, such as glycidyl acrylate and glycidyl methacrylate. Preferred further monomers are the esters with $C_1$-$C_{10}$-alkanols of acrylic acid and of methacrylic acid.

In a further embodiment, the linear polymer may be a block polymer comprising a block of polyethylene glycol or of at least one polar ethylenically unsaturated monomer. The molar mass $M_n$ is usually in the range of 200-10 000 g/mol, preferably between 300 and 2000 g/mol, and can be determined by GPC. The block polymer may be of the A-B or A-B-A type, preferably A-B type. The preparation of block polymers of these types is common knowledge. Suitable and preferred polar ethylenically unsaturated monomers are as specified above. Examples of a block of polyethylene glycol are polyethylene glycol or polyethylene glycol monoalkyl ethers having a molar mass $M_n$ of 200 to 10 000 g/mol. Examples of a block of at least one polar ethylenically unsaturated monomer are polyvinylpyrrolidone or poly (meth)acrylic acid or polyethylene glycol monomethyl ether (meth)acrylate. The other block in each case may be formed from polymer blocks from the prior art. The other block is preferably nonpolar; for example, it is formed from caprolactone or propylene oxide. In a further embodiment, the other block comprises polyesters (for example based on a dicarboxylic acid and a diol), polyamide (for example based on a dicarboxylic acid and a diamine), polycarbonate, polyurethane or polyurea. Preferred block polymers are polyethylene glycol-block-polycaprolactone and polyethylene glycol monomethyl ether-block-polycaprolactone and polypropylene glycol-block-polyethylene glycol.

In a further embodiment, the linear polymer may be a polycondensate comprising polyethylene glycol. In the context of the present invention, the term "polycondensate" also includes polyaddition products. Examples of polyethylene glycol are polyethylene glycol or polyethylene glycol monoalkyl ethers having a molar mass $M_n$ of 200 to 10 000 g/mol. Examples of polycondensates are polyethers, polyamides, polyimides, polyesters, polycarbonates, polyurethanes and polyureas, preferably polyethers and polyesters. A preferred polycondensate is a polyether based on $C_3$-$C_{24}$ alkylene oxide, particularly propylene oxide, and a polyester based on hydroxycarboxylic acid compounds, dialcohol compounds or diacid compounds, particularly hydroxycarboxylic acid compounds. Preferred hydroxycarboxylic acid compounds are lactones, especially $C_4$ to $C_{18}$-alkyl lactones, most preferably ε-caprolactone.

In a further embodiment, the linear polymer may be a polyethylene glycol, in which case the polyethylene glycol is joined to the polyurea via a linker. The linker is preferably a polyisocyanate. Examples of polyethylene glycol are polyethylene glycol or polyethylene glycol monoalkyl ethers having a molar mass $M_n$ of 200 to 10 000 g/mol, preferably 300-2000 g/mol. The polyethylene glycol is preferably a polyethylene glycol mono-$C_1$-$C_{18}$-alkyl ether, especially a polyethylene glycol monomethyl ether.

Comb-type polymers are understood here to mean comb polymers which typically comprise relatively long side chains of virtually equal length, preferably aliphatic side chains, at more or less regular intervals on a linear main chain. The molar mass $M_n$ is usually in the range from 500 to 100 000 g/mol and can be determined by GPC. The comb-type polymer preferably comprises polyalkylene glycol mono(meth)acrylate or allyl alcohol alkoxylate (such as polyethylene glycol allyl ether) in polymerized form, preferably polyethylene glycol monoalkyl ether (meth)acrylate with a molar mass $M_n$ of 100 to 5000 g/mol. The comb polymer more preferably comprises polyethylene glycol monomethyl ether acrylate or polyethylene glycol monomethyl ether methacrylate with a molar mass $M_n$ of in each case 100 to 3000 g/mol, preferably 200 to 1500 g/mol. In addition to polyalkylene glycol mono(meth)acrylate or allyl alcohol alkoxylates, the comb polymer may comprise any desired copolymerizable ethylenically unsaturated monomers. Preferred additional monomers are nonpolar monomers and/or the aforementioned polar ethylenically unsaturated monomers. Preferred nonpolar monomers are $C_1$-$C_{20}$-alkyl (meth)acrylates or vinylaromatics having up to 20 carbon atoms. Examples comprise methyl (meth)acrylate, ethyl (meth)acrylate, n-butyl (meth)acrylate, 2-ethylhexyl (meth)acrylate, lauryl (meth)acrylate or 4-t-butylcyclohexyl (meth)acrylate. Useful vinylaromatic compounds include, for example, vinyltoluene, α-butylstyrene, 4-n-butylstyrene, 4-n-decylstyrene or styrene. Preferred additional monomers are methyl (meth)acrylate, lauryl acrylate, stearyl acrylate, styrene, vinylpyrrolidone or mixtures thereof.

The linear or comb-type polymer can be prepared by commonly known methods (for example from U.S. Pat. No. 5,556,918 and EP 742 238). In one embodiment, the linear polymer, which is a homopolymer or random copolymer comprising a polar ethylenically unsaturated monomer, the block polymer comprising a block of polyethylene glycol or based on at least one polar ethylenically unsaturated monomer, and the comb polymer, are prepared by free-radically initiated solution polymerization of the monomers in the presence of an initiator and if appropriate of a regulator. Preference is given to using an initiator which, when it decomposes, forms a hydroxyl radical (OH radical), and/or a regulator which comprises an OH group or an $NH_2$ group. These OH or $NH_2$ groups can be used later as the linker-reactive group.

Suitable initiators are organic hydroperoxides such as tert-butyl hydroperoxide, tetrahydrofuran hydroperoxide, cumene hydroperoxide or 2,2'-azobis(2-methyl-N-(2-hydroxyethyl)propionamide). Suitable regulators are aminoalcohols, aminophenols and especially thioalkanols such as 3-hydroxypropanethiol, 3-mercapto-1,2-propanediol, 2-hydroxyethyl 3-mercaptopropionate, and in particular 2-hydroxyethanethiol (mercaptoethanol). When such a regulator is used, the polymerization can also be performed in the presence of a conventional initiator, for example of a conventional azo initiator or of an organic peroxide such as azobis(isobutyronitrile), di-(tert-butyl) peroxide, didecanoyl peroxide, dibenzoyl peroxide, tert-butyl peracetate or tert-butyl 2-methylperpropionate. When the polymerization is performed in the presence of one of the aforementioned regulators, the regulator will generally be used in an amount of 0.1 to 12% by weight, frequently 0.2 to 8% by weight and especially 0.5 to 5% by weight, based on the total amount of the monomers. Initiators are generally used in an amount of 0.05 to 5% by weight, frequently 0.1 to 4% by weight and more preferably in an amount of 0.2 to 3% by weight, based on the monomers to be polymerized. For further details, reference is made especially to page 3 of EP 742 238, whose disclosure is incorporated by reference.

The linear or comb-type polymers are preferably joined to the dedritic polyurea with the aid of a difunctional linker. Usually, the linker is first bonded covalently to the linear or comb-type polymer, in order then to couple the linker-containing polymer onto the dendritic polyurea. In order that the linker-containing polymer can be prepared, the starting polymer usually comprises a group which can react with the linker (linker-reactive group). The mean number of linker-reactive groups is generally not more than two, and is preferably in the range from 0.3 to 1.8, in particular in the range from 0.5 to 1.5 and especially in the range from 0.6 to 1.4 per polymer molecule. The linker-reactive group may be arranged within the polymer chain or is preferably at the end of the polymer chain.

In the case of a linear polymer which is a homopolymer or random copolymer comprising a polar ethylenically unsaturated monomer, a block polymer comprising a block of polyethylene glycol or based on at least one polar ethylenically unsaturated monomer, or of a comb polymer, the linker-reactive group can be introduced as described above by means of a suitable initiator and/or regulator. Alternatively, the linker-reactive group can be introduced at the chain end in a controlled manner by means of a controlled free-radical reaction according to the prior art (such as Atom Transfer Radical Polymerization (ATRP), Reversible Addition Fragmentation Chain Transfer Polymerization (RAFT), or Nitroxide Mediated Polymerization (NMP)). It is equally possible that a functional group in the polymer chain is used as the linker-reactive group, for example one of possibly several OH groups of a polymerized hydroxyethyl (meth)acrylate.

In the case of a polycondensate comprising polyethylene glycol, a linker-reactive group can be obtained at the chain end of the polycondensate by means of a suitable stoichiometry and use of a monofunctional monomer. The linker-reactive group is preferably obtained by ring-opening polymerization of a lactone, such that exactly one functional hydroxyl group forms at the chain end.

In the case of a polyethylene glycol, the linker-reactive group used may be a hydroxyl group at the chain end. Preference is given to polyethylene glycol monoalkyl ethers which have exactly one linker-reactive group at the chain end.

In general, useful difunctional linkers include reactive polyfunctional compounds with at least two reactive groups. Preferred linkers are polyisocyanates having a functionality based on the isocyanate groups of at least 1.5, in particular 1.5 to 4.5 and especially 1.8 to 3.5, comprise aliphatic, cycloaliphatic and aromatic di- and polyisocyanates, and the isocyanurates, allophanates, uretdiones and biurets of aliphatic, cycloaliphatic and aromatic diisocyanates. The polyisocyanates preferably have an average of 1.8 to 3.5 isocyanate groups per molecule. Examples of suitable polyisocyanates are aromatic diisocyanates such as tolylene 2,4-diisocyanate, tolylene 2,6-diisocyanate, commercially available mixtures of tolylene 2,4- and 2,6-diisocyanate (TDI), phenylene diisocyanate, 3,3'-diphenyl-4,4'-biphenylene diisocyanate, 4,4'-biphenylene diisocyanate, 4,4'-diphenylmethane diisocyanate, 2,4'-diphenylmethane diisocyanate, 3,3'-dichloro-4,4'-biphenylene diisocyanate, cumene 2,4-diisocyanate, 1,5-naphthalene diisocyanate, p-xylylene diisocyanate, p-phenylene diisocyanate, 4-methoxy-1,3-phenylene diisocyanate, 4-chloro-1,3-phenylene diisocyanate, 4-ethoxy-1,3-phenylene diisocyanate, 2,4-dimethylene-1,3-phenylene diisocyanate, 5,6-dimethyl-1,3-phenylene diisocyanate, 2,4-diisocyanatodiphenyl ether, aliphatic diisocyanates such as ethylene diisocyanate, ethylidene diisocyanate, propylene 1,2-diisocyanate, 1,6-hexamethylene diisocyanate (HDI), 1,4-tetramethylene diisocyanate, 1,10-decamethylene diisocyanate, and cycloaliphatic diisocyanates such as isophorone diisocyanate (IPDI), cyclohexane 1,2-diisocyanate, cyclohexane 1,4-diisocyanate and bis(4,4'-isocyanato-cyclohexyl)methane. Among the polyisocyanates, preference is given to those whose isocyanate groups are of different reactivity, such as tolylene 2,4-diisocyanate, tolylene 2,6-diisocyanate, 2,4'-diphenylmethane diisocyanate, isophorone diisocyanate, or mixtures of these compounds.

The reaction conditions for the reaction with the polyisocyanate depend on the type of linker-reactive group of the linear or comb-type or of the dendritic polymer. The reaction can in principle be carried out in the melt or in an organic solvent. If the linker-reactive group of the linear or comb-type polymer is a hydroxyl group, reactions with the linker preferably take place in an aprotic polar organic solvent or mixtures of such solvents. Examples are ketones (for example acetone), butyl acetate, tetrahydrofuran (THF), xylene, chlorobenzene, dimethyl sulfoxide (DMSO) or dimethylformamide (DMF). Preferred solvents are butyl acetate, tetrahydrofuran, xylene and acetone. The reaction is effected typically at elevated temperatures, the temperature also being guided by the boiling temperature of the solvent selected. The polyisocyanate can be reacted with the first component at 20 to 80° C., but if desired also to 100° C., if the first component has a hydroxyl group as linker-reactive group.

The reaction of the further isocyanate group with the linker-reactive group of the dendritic polyurea takes place preferably at temperatures of −20 to 40° C., provided the linker-reactive groups of the polyurea are amino groups. In this case the reaction may be carried out in turn in the melt or in an organic solvent. In contrast to the reaction with the first component (provided it possesses a hydroxyl group as linker-reactive group), it is now also possible to use alcohols as solvents, in addition to the solvents already listed, since the reaction of the remaining isocyanate group with an amino group of the polymer proceeds more rapidly than the competing reaction with a hydroxyl group of the alcoholic solvent component. Preferred alcohols are methanol, ethanol, isopropanol, n-propanol, n-butanol, isobutanol, and tert-butanol. Especially preferred solvents for the reaction of the second isocyanate group with the polyurea are solvent mixtures of butyl acetate, tetrahydrofuran, xylene or acetone (resulting from the first reaction) and one of the above-listed alcohols (in which the HB polyurea can be dissolved to particularly good effect). In one specific embodiment the joining of the linear or comb-type polymers to the dendritic polyurea core is carried out without solvent in the melt.

The reaction can be effected in an equimolar manner, which means that the quantitative ratio is selected such that 1 mol of diisocyanate is used per mole of hydroxyl group to be converted in the functionalizing reagent or in the linear or comb-type polymer. Preference is given to working with a slight (e.g. 0 to 15 mol %) excess of the hydroxyl groups, in order to reduce the amount of unconverted diisocyanate. When the free-radical copolymer is OH-functionalized by means of an initiator or regulator, the diisocyanate is reacted in an equimolar amount or in a slight deficiency relative to the OH groups introduced in this way. In the case of symmetric diisocyanates (such as HDI), it may also be advisable to use an excess of diisocyanate and then to remove the excess by distillation.

Preference is given to performing the reaction in the presence of a catalyst. Suitable catalysts are, for example, tertiary amines, for example triethylamine, tri-n-propylamine, N-methylpyrrolidine, N-methylpiperidine and diazabicyclooctane (DABCO), zinc carboxylates, bismuth carboxylates, titanium alkoxides, organotin compounds, especially dialkyltin(IV) salts of aliphatic carboxylic acids such as dibutyltin dilaurate and dibutyltin dioctoate, tin(II) dialkanoates such as tin dioctoate, and cesium salts such as cesium acetate. In one embodiment, zinc carboxylates, bismuth carboxylates, titanium alkoxides are particularly suitable, the carboxylates preferably being $C_1$-$C_{20}$ carboxylates (such as formate, acetate, propionate, hexanoate, octanoate or neodecanoate). The catalyst can be used in amounts of 50 to 50 000 ppm, preferably 100 to 5000 ppm, based on the overall solids.

The reaction with the hydroxyl groups is typically performed at elevated temperatures in the range from 40 to 120° C. However, the reaction with amino groups, especially with those of the dendritic polyurea core, is preferably effected at temperatures of −20 to 40° C. Which temperature is selected in the individual case depends on the type of organic solvent used. The solvent can subsequently be removed by distillation.

Typically, the reaction will be performed in such a way that the component which is to be functionalized with isocyanate groups (for example the linear or comb-type polymer) is first reacted with the diisocyanate in the presence of the catalyst and optionally of a solvent until the isocyanate value in the reaction mixture has fallen by half. In the case of use of a slight hydroxyl group excess, reaction is continued until the theoretical end value corresponds to the complete conversion of the hydroxyl groups. This can be determined, for example, by titrimetric means in a known manner. This is then followed by the addition of the other component (for example hyperbranched polyurea having amino groups). The molar ratio of dendritic polyurea to the sum of linear polymer and comb-type polymer is in the range from 1:1 to 1:100, preferably 1:1 to 1:50, more preferably 1:1 to 1:25. The reaction is continued until the isocyanate value has fallen to zero.

The composition of the invention is obtainable by bringing the amphiphile and the active ingredient whose solubility in water at 20° C. is not more than 10 g/L into contact, the amphiphile comprising a dendritic polyurea which is joined to at least one linear or comb-type polymer, and the joining is effected via a difunctional linker, if the linear polymer is composed of a polyalkylene oxide. The components can be brought into contact by methods which are common knowledge, such as mixing, emulsifying or suspending.

The weight ratio of active ingredient to amphiphile is usually in the range from 100:1 to 1:100, preferably 10:1 to 1:50, more preferably 2:1 to 1:25. The active ingredient may be in dissolved form or in solid, particulate form. The active ingredient particles may be crystalline or amorphous. The particle size may be 1 nm to 10 µm. The composition may be a solution, emulsion, suspension or suspoemulsion of the active ingredient. The composition of the invention is preferably an aqueous composition. Preferably it comprises at least 40%, more preferably at least 60%, and more particularly at least 80% by weight of water. The composition typically comprises not more than 99% by weight of water.

The composition of the invention may comprise formulating assistants, the choice of assistants being guided typically by the specific application form and/or active ingredient. Examples of suitable formulating assistants are solvents, solid carriers, surface-active substances (such as surfactants, protective colloids, wetting agents, and stickers), organic and inorganic thickeners, bactericides, antifreeze agents, defoamers, colorants if desired, and adhesives (e.g., for seed treatment).

Surface-active substances contemplated (adjuvants, wetting agents, stickers, dispersants or emulsifiers) include the alkali metal, alkaline earth metal, and ammonium salts of aromatic sulfonic acids, e.g., those of lignosulfonic (Borresperse® products, Borregaard, Norway), phenolsulfonic, naphthalenesulfonic (Morwet® products, Akzo Nobel, USA), and dibutylnaphthalenesulfonic (Nekal® products, BASF, Germany) acid, and also of fatty acids, alkyl- and alkylarylsulfonates, alkyl, lauryl ether, and fatty alcohol sulfates, and also salts of sulfated hexa, hepta-, and octadecanols and also of fatty alcohol glycol ethers, condensation products of sulfonated naphthalene and its derivatives with formaldehyde, condensation products of naphthalene or of naphthalenesulfonic acids with phenol and formaldehyde, polyoxyethylene octylphenol ethers, ethoxylated isooctylphenol, octylphenol or nonylphenol, alkyllphenyl and tributylphenyl polyglycol ethers, alkylaryl polyether alcohols, isotridecyl alcohol, fatty alcohol ethylene oxide condensates, ethoxylated castor oil, polyoxyethylene or polyoxypropylene alkyl ethers, lauryl alcohol polyglycol ether acetate, sorbitol esters, lignin-sulfite waste liquors, and also proteins, denatured proteins, polysaccharides (e.g., methylcellulose), hydrophobically modified starches, polyvinyl alcohol (Mowiol® products, Clariant, Switzerland), polycarboxylates (Sokalan® products, BASF, Germany), polyalkoxylates, polyvinylamine (Lupamin® products, BASF, Germany), polyethyleneimine (Lupasol® products, BASF, Germany), polyvinylpyrrolidone and copolymers thereof.

Suitable surfactants include, in particular, anionic, cationic, nonionic, and amphoteric surfactants, block polymers, and polyelectrolytes. Suitable anionic surfactants are alkali metal, alkaline earth metal or ammonium salts of sulfonates, sulfates, phosphates or carboxylates. Examples of sulfonates are alkylarylsulfonates, diphenylsulphonates, alpha-olefinsulfonates, sulfonates of fatty acids and oils, sulfonates of ethoxylated alkylphenols, sulfonates of condensed naphthalenes, sulfonates of dodecyl and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates and carboxylated alcohol or alkylphenol ethoxylates.

Suitable nonionic surfactants are alkoxylates, N-alkylated fatty acid amides, amine oxides, esters or sugar-based surfactants. Examples of alkoxylates are compounds, such as alcohols, alkylphenols, amines, amides, arylphenols, fatty acids or fatty acid esters, which have been alkoxylated. For the alkoxylation it is possible to use ethylene oxide and/or propylene oxide, preferably ethylene oxide. Examples of N-alkylated fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose esters and glucose esters, or alkylpolyglucosides. Suitable cationic surfactants are quaternary surfactants, examples being quaternary ammonium compounds having one or two hydrophobic groups, or salts of long-chain primary amines. Suitable amphoteric surfactants are alkylbetaines and imidazolines. Suitable block polymers are block polymers of A-B or A-B-A type, comprising blocks of polyethylene oxide and polypropylene oxide, or of A-B-C type, comprising alkanol, polyethylene oxide, and polypropylene oxide. Suitable polyelectrolytes are polyacids or polybases. Examples of polyacids are alkali metal salts of polyacrylic acid. Examples of polybases are polyvinylamines or polyethylenamines.

The composition of the invention may comprise large amounts of surface-active substances and surfactant. It may comprise 0.1% to 40%, preferably 1% to 30% and more particularly 2% to 20% by weight in total amount of surface-active substances and surfactants, based on the total amount of the composition.

Examples of adjuvants are organically modified polysiloxanes, such as BreakThruS 240®; alcohol alkoxylates, such as Atplus®245, Atplus®MBA 1303, Plurafac®LF, and Lutensol® ON; EO-PO block polymers, e.g., Pluronic® RPE 2035 and Genapol® B; alcohol ethoxylates, e.g., Lutensol® XP 80; and sodium dioctylsulfosuccinate, e.g., Leophen® RA.

Examples of thickeners (i.e., compounds which give the composition a modified rheology, i.e., high viscosity in the state of rest and low viscosity in the mobile state) are polysaccharides and also organic and inorganic layer minerals such as xanthan gum (Kelzan®, CP Kelco), Rhodopol® 23 (Rhodia) or Veegum® (R.T. Vanderbilt) or Attaclay® (Engelhard Corp.).

In one preferred embodiment the active compound is a pesticide and the compositions of the invention are in the form of an agrochemical formulation. Suitable agrochemical formulations are water-soluble concentrates (SL, LS), redispersible concentrates (DC), emulsifiable concentrates (EC), emulsions (EW, EO, ES, ME), suspensions (SC, OD, FS) or suspoemulsions (SE). The composition preferably takes the form of an emulsifiable concentrate (EC), a suspension concentrate (SC), a water-soluble concentrate (SL), a solution for seed treatment (LS), or a redispersible concentrate (DC).

The agrochemical formulation is usually diluted prior to application, to prepare what is known as a tankmix. Suitable agents for the dilution include mineral oil fractions of moderate to high boiling point, such as kerosene or diesel oil, and also coal tar oils and oils of vetable or animal origin, aliphatic, cyclic, and aromatic hydrocarbons, e.g., toluene, xylene, paraffin, tetrahydronaphthalene, alkylated naphthalenes or derivatives thereof, methanol, ethanol, propanol, butanol, cyclohexanol, cyclohexanone, isophorone, strongly polar solvents, e.g., dimethyl sulfoxide, N-methylpyrrolidone or water. It is preferred to use water. It is also possible to add the amphiphile only to the actual tankmix. In this embodiment the composition of the invention is in the form of a tankmix.

The diluted composition is typically applied by spraying or nebulizing. To the tankmix it is possible to add oils of various types, wetting agents, adjuvants, herbicides, bactericides or fungicides immediately prior to application (tankmix). These agents may be admixed to the compositions of the invention in a weight ratio of 1:100 to 100:1, preferably 1:10 to 10:1. The concentration of pesticide in the tankmix may be varied within relatively wide ranges. Concentrations are in general between 0.0001% and 10%, preferably between 0.01% and 1%. In the case of application in crop protection, and depending on the nature of the desired effect, the application rates are between 0.01 and 2.0 kg of active ingredient per ha.

The agrochemical formulations can be used to control phytopathogenic fungi and/or unwanted plant growth and/or unwanted insect or mite infestation and/or to regulate the growth of plants, the composition then being caused to act on the respective pests, their habitat, or the plants to be protected from the respective pest, the soil, and/or on unwanted plants and/or on the crop plants and/or on their habitat. The agrochemical formulations can also be used to control unwanted insect or mite infestation on plants and/or to control phytopathogenic fungi and/or to control unwanted plant growth, with seeds of crop plants being treated with the composition.

The invention also provides an amphiphile comprising a dendritic polyurea, the dendritic polyurea being joined to at least one linear or comb-type polymer, and the joining being effected via a difunctional linker, if the repeat units of the linear polymer are composed of polymerized alkylene oxide. The polyurea is preferably composed of a polyisocyanate and a hydrophobic polyamine, and, apart from nitrogen in the form of primary amino groups, the hydrophobic polyamine preferably has no further heteroatoms.

A preferred amphiphile comprises a dendritic polyurea which is joined to at least one linear or comb-type polymer, wherein the linear polymer is
a) a homopolymer or random copolymer comprising a polar ethylenically unsaturated monomer,
b) a block polymer comprising a block of polyethylene glycol or based on a polar ethylenically unsaturated monomer,
c) a polycondensate comprising polyethylene glycol, or
d) a polyethylene glycol,
the polyethylene glycol d) being joined to the polyurea via a difunctional linker.

Suitable and preferably linear or comb-type polymers are as described above. With particular preference the linear polymer is one of the aforementioned polymers a), b) or c). In another particularly preferred embodiment the linear polymer is one of the aforementioned polymers a), c) or d). With very particular preference the linear polymer is one of the aforementioned polymers a) or c). With especial preference the comb-type polymer comprises polyethylene glycol mono(meth)acrylate in polymerized form. A preferred linker is a polyisocyanate. Other preferred embodiments of the dendritic polyurea have been described above.

The invention also provides a process for preparing the amphiphile of the invention, by
a) reacting the polyurea with the linear or comb-type polymer, or
b) reacting the polyurea with a monomer which by ring-opening polymerization is able to form part of the linear or comb-type (preferably linear) polymer.
Preference is given to variant a).

Suitable monomers for variant b) are, for example, lactones, lactides or oxazolidines, preferably ε-caprolactone. Following the ring-opening polymerization in variant b), the resulting part-polymer is typically reacted further in order to give the amphiphile of the invention. For example, the further reaction may be a conventional alkoxylation (e.g., with ethylene oxide).

According to preparation variant a), the linear or comb-type polymer and a difunctional linker are reacted. Preferred difunctional linkers and reaction conditions are as described above. According to a particularly preferred variant a), the amphiphile is obtainable by
i) providing the dendritic polyurea and the linear or comb-type polymer, and then
ii) joining the components with the difunctional linker.

With particular preference the amphiphile is obtained in this way. The difunctional linker is preferably a diisocyanate.

Advantages of the present invention are that a high concentration of active compound can be brought into solution, that the preparation of the amphiphile from pre-prepared polymers can be accomplished very easily and industrially by means of a linker, that the linear or comb-type polymers (more particularly the random copolymers and the polar homopolymers and also polyethylene glycol) are very easy to obtain and can even be optimized for particular amphiphiles, or that the amphiphile itself is water-soluble or water-dispersible.

As compared with the direct alkoxylation of the dendritic polyurea, the process of the invention affords the advantages that
i) the polyurea can be reacted readily in alcohols as solvents with the linker-modified polyethylene glycol, since the amino group has a higher reactivity with respect to the isocyanate group than does the hydroxyl group of the solvent; alcohols as solvents for the dendritic polyureas are necessary, since the polyureas do not dissolve in common, less polar organic solvents (acetone, tetrahydrofuran, butyl acetate, xylene, toluene); the use of toxic or high-boiling dipolar-aprotic solvents such as dimethylformamide or dimethyl sulfoxide leads to secondary reactions (KOH catalyst decomposes solvents).
ii) The polyurea is functionalized with PEG chains of the same chain length (which are obtainable in "prefabricated" form with an extremely narrow MW distribution); in the case of the alkoxylation, in contrast, the problem occurs that the initial reaction of an amino group with 2 EO units leads to an aminodiol group, which is then simultaneously able itself (albeit more slowly) to undergo further reaction with EO, producing chains of different lengths (also owing to the steric conditions in the polymer, etc.).
iii) The amphiphile prepared in accordance with the invention can be tailored in its amphiphilicity and in its applications properties by the linker itself (e.g., isophorone diisocyanate linker increases hydrophobic fraction of the resulting amphiphile and thus improves the take-up of the active ingredient via hydrophobic interactions).

Further advantages are that the bioavailability of the active ingredients is increased, that the systemic effect of the active agrochemical ingredients in the case of foliar uptake is increased, that even sparingly soluble active agrochemical ingredients can now be formulated in dissolved form, for example, as SL (water-soluble concentrate) or LS (solution for seed treatment), that the distribution of the active agrochemical ingredients in the spray solution is improved, and that the reusable packaging of the active ingredients and the application devices (e.g., the spray devices for pesticides) can be cleaned more efficiently with water.

The examples which follow illustrate the invention without restricting it.

EXAMPLES

Basonat® HI 100: Polyisocyanurate based on hexamethylene diisocyanate, NCO content in accordance with DIN EN ISO 11909 21.5% by weight, viscosity at 23° C. in accordance with DIN EN ISO 3219 3500 mPas, commercially obtainable from BASF SE.
DBTL: Di-n-butyltin dilaurate
IPDI: Isophorone diisocyanate
PEGMEMA 475: Polyethylene glycol monomethyl ether methacrylate (M=475 g/mol)
PEGMENA 1100: Polyethylene glycol monomethyl ether methacrylate (M=100 g/mol)
AIBN: Azobis(isobutyronitrile)

The hyperbranched polymers were analyzed by gel permeation chromatography using a refractometer as detector. The mobile phase used was hexafluoroisopropanol, while the standard used for determining the molecular weight was polymethyl methacrylate (PMMA). The amine numbers (the primary amine number is always given in the following text) were determined in accordance with DIN EN 13717. The molar masses of the polymers of the invention were determined arithmetically from the number-average molecular weight of the parent hyperbranched core molecule, its amine number, and the degree of functionalization selected (stoichiometric ratio of NCO groups of functional linear polymers to available amine groups of core molecule) assuming a quantitative addition reaction of the linker-reactive groups to the linker.

Synthesis Example 1

Hyperbranched Polyurea Having Terminal Amino Groups (A.1)

With dry nitrogen gassing, 135.8 g of Basonat® HI 100 were introduced and were heated to 80° C. with stirring. Then, with continual stirring, over a period of 2 hours, 104.5 g of anhydrous n-butanol were added at a rate such that the temperature of the reaction mixture did not exceed 80° C. After the end of addition, stirring was continued at 80° C. for a further hour. The batch was then cooled to 60° C. and admixed with 59.7 g of isophoronediamine and 0.1 g of potassium hydroxide (in solution in 2.0 ml of n-butanol). The reaction mixture was subsequently stirred at 150° C. for 11.5 hours, before a further 0.2 g of potassium hydroxide was added, followed by stirring at 150° C. for 2 hours more. Over the reaction time, the consumption of amine in the reaction mixture was monitored by titration with 0.1N HCl, and in this way the conversion was determined as a percentage of the full conversion theoretically possible. When a conversion of 60% was attained, the reaction was terminated by cooling the reaction mixture to RT. The n-butanol-comprising polymer A.1 (Mn=1710 g/mol; Mw=3860 g/mol; amine number: 36 mg KOH/g polymer) was obtained in the form of a yellow-colored liquid of high viscosity which was not water-soluble.

Synthesis Example 2

Hyperbranched Polyurea Having Terminal Amino Groups (A.2)

Stage 1 (A.2a): With dry nitrogen gassing, 1499.1 g of Basonat® HI 100 were introduced and were heated to 80° C. with stirring. Then, with continual stirring, over a period of 3.0 hours, 1155.9 g of n-butanol were added at a rate such that the temperature of the reaction mixture did not exceed 80° C. After the end of the addition, stirring was continued at 78° C. for 30 minutes, before the reaction mixture was cooled to RT.

Stage 2 (A.2): With dry nitrogen gassing, 146.4 g of the reaction product A.2a and 36.4 g of isophoronediamine were introduced. Following the addition of 0.1 g of potassium hydroxide (in solution in 2 ml of n-butanol) as catalyst, the reaction mixture was heated to 150° C. with stirring and was stirred at this temperature for 12 hours, after which the reaction was terminated by cooling to RT.

The polymer A.2 (Mn=3600 g/mol; Mw=12 100 g/mol; amine number: 25 mg KOH/g polymer) was obtained in the form of a yellow-colored liquid of high viscosity which was not water-soluble.

Synthesis Example 3

Hyperbranched Polyurea Having Terminal Amino Groups (A.3)

Stage 1 (A.3a): With dry nitrogen gassing, 1499.1 g of Basonat® HI 100 were introduced and were heated to 80° C. with stirring. Then, with continual stirring, over a period of 3.0 hours, 1155.9 g of n-butanol were added at a rate such that the temperature of the reaction mixture did not exceed 80° C. After the end of the addition, stirring was continued at 78° C. for 30 minutes, before the reaction mixture was cooled to RT.

Stage 2 (A.3): 240 g of the reaction product A.3a and 59.7 g of isophoronediamine were introduced and admixed with 0.02 g of DBTL as catalyst. The reaction mixture was heated to 160° C. with stirring and was stirred at this temperature for 2 hours, with n-butanol released during the reaction being separated off by distillation. During this time, the consumption of amine in the reaction mixture was monitored via titration with 0.1N HCl, and in this way the conversion was determined as a percentage of the full conversion theoretically possible. When a conversion of 47% had been reached, the reaction was terminated by cooling to RT, and the product was diluted with 100 ml of n-butanol during the cooling process.

The n-butanol-comprising polymer A.3 (Mn=2600 g/mol; Mw=10 200 g/mol; amine number: 55 mg KOH/g polymer) was obtained in the form of a yellow-colored liquid of high viscosity which was not water-soluble.

Synthesis Example 4

Hyperbranched Polyurea Having Terminal Amino Groups (A.4)

With dry nitrogen gassing, 129.3 g of Basonat® HI 100 were introduced and were heated to 80° C. with stirring. Then, with continual stirring, over a period of 1.5 hours, 99.6 g of n-butanol were added at a rate such that the temperature of the reaction mixture did not exceed 80° C. After the end of addition, stirring was continued at 80° C. for a further 30 minutes. The batch was then cooled to 60° C., the reflux condenser was switched for a descending condenser with collecting vessel, and the reaction mixture was admixed with 71.1 g of isophoronediamine and 0.05 g of DBTL. The reaction mixture was heated to 150° C. with stirring and was stirred at that temperature for 1.5 hours, with n-butanol given off during the reaction being separated off by distillation. Over the reaction time, the consumption of amine in the reaction mixture was monitored by titration with 0.1N HCl, and in this way the conversion was determined as a percentage of the full conversion theoretically possible. When a conversion of 35% was attained, the reaction was terminated by cooling the reaction mixture to RT, and diluting it with 100 ml of n-butanol during the cooling process. The n-butanol-comprising polymer A.4 (Mn=2200 g/mol; Mw=6600 g/mol; amine number: 33 mg KOH/g polymer) was obtained in the form of a yellow-colored liquid of high viscosity which was not water-soluble.

Synthesis Example 5

Copolymer Based on a Hydrophobic Hyperbranched Polyurea Core (A.1) and Linear Peg Chains, Degree of Functionalization 100% (A.5)

Stage 1 (A.5a): 123.5 g of polyethylene glycol monomethyl ether (Mn=500 g/mol) were introduced and were freed from residues of water at 80° C. under reduced pressure. After cooling to room temperature, the batch was placed under nitrogen and the polymer was dissolved in 123.5 g of butyl acetate. Then 50.0 g of isophorone diisocyanate were added and the mixture was heated to 50° C. Through addition of 19 mg of zinc neodecanoate in solution in 1 ml of butyl acetate, the reaction was initiated and was run, over the course of 3.5 hours at 50° C., to an NCO content of 2.87%. Thereafter the reaction was ended by cooling to −20° C. The reaction product A.5a was used directly, without further work-up, in stage 2.

Stage 2 (A.5): 4.0 g of the polyurea core A.1 were introduced, were dissolved under nitrogen in 36.0 g of isobutanol, and were admixed with 3.9 g of reaction mixture A.5a. Then the batch was stirred at 25° C. for 72 hours. Following the complete reaction of all the NCO groups (NCO content 0%), the solvent was removed under reduced pressure. Finally this gave the linear-dendritic copolymer A.5 (Mn=249 g/mol) in the form of a yellow-colored liquid of high viscosity which was fully water-soluble.

Synthesis Example 6

Copolymer Based on a Hydrophobic Hyperbranched Polyurea Core (A.2) and a Comblike PMMA-co-PS-co-PEGMEMA Copolymer, Degree of Functionalization 100% (A.6)

Stage 1 (A.6a): 250.0 g of tetrahydrofuran were introduced under nitrogen and then heated under reflux. Over the course of 2 hours, a mixture 1 composed of 117.1 g of methyl methacrylate, 44.8 g of styrene and 315.7 g of PEGMEMA 1100, and also, at the same time, over the course of 4 hours, a mixture 2, composed of 5.4 g of AIBN and 17.0 g of mercaptoethanol, in solution in 250.0 g of THF, were supplied slowly to the batch with the aid of two metering pumps. After the end of the addition of mixture 2, the reaction mixture was heated under reflux for a further 16 hours. Subsequent monitoring of the residual monitors by means of GC indicated an MMA fraction of <1%, and so the batch was cooled and the product A.6a (Mn=2200 g/mol) was used directly further in stage 2.

Stage 2 (A.6b): 200.0 g of the reaction mixture A.6a were introduced and were freed from the THF solvent under reduced pressure. After cooling to room temperature, the batch was placed under nitrogen and the residue was dissolved in 97.0 g of butyl acetate. Then 8.78 g of isophorone diisocyanate were added and the mixture was heated to 50° C. Through addition of 10 mg of zinc neodecanoate in solution in 1 ml of butyl acetate, the reaction was initiated and was run, over the course of a total of 14 hours at 50° C., to an NCO content of 0.71%. Thereafter the reaction was ended by cooling to −20° C. The reaction product A.6b was used directly, without further work-up, in stage 3.

Stage 3 (A.6): 3.0 g of the polyurea core A.2 were introduced, were dissolved under nitrogen in 27.0 g of isobutanol, and were admixed with 9.0 g of reaction mixture A.6b. Then the batch was stirred at 25° C. for 48 hours. Following the complete reaction of the NCO groups (NCO content 0%), the solvent was removed under reduced pressure. Finally this gave the linear-dendritic copolymer A.6 (Mn=7120 g/mol) in the form of a yellow-colored liquid of high viscosity which was fully water-soluble.

Synthesis Example 7

Copolymer Based on a Hydrophobic Hyperbranched Polyurea Core (A.3) and a Comblike PVP-co-P Lauryl Acrylate-Co-PEGMEMA Copolymer, Degree of Functionalization 100% (A.7)

Stage 1 (A.7a): 100.0 g of tetrahydrofuran were introduced under nitrogen and then heated under reflux. Over the course of 3 hours, a mixture 1 composed of 155.9 g of lauryl acrylate, 144.2 g of N-vinylpyrrolidone and 163.3 g of PEGMEMA 475, in solution in 200.0 g of THF and also, at the same time, over the course of 4 hours, a mixture 2, composed of 8.8 g of AIBN and 27.8 g of mercaptoethanol, in solution in 200.0 g of THF, were supplied slowly to the batch with the aid of two metering pumps. After the end of the addition of mixture 2, the reaction mixture was heated under reflux for a further 18 hours. Subsequent monitoring of the residual monomers by means of GC indicated a lauryl acrylate fraction of <1%, and so the batch was cooled and the product A.7a (Mn=1000 g/mol) was used directly further in stage 2.

Stage 2 (A.7b): 278.4 g of the reaction mixture A.7a were introduced and were freed from the THF solvent under reduced pressure. After cooling to room temperature, the batch was placed under nitrogen and the residue was dissolved in 140.0 g of butyl acetate. Then 20.0 g of isophorone diisocyanate were added and the mixture was heated to 50° C. Through addition of 21 mg of zinc neodecanoate in solution in 1 ml of butyl acetate, the reaction was initiated and was run, over the course of a total of about 12 hours at 50° C., to an NCO content of 1.06%. Thereafter the reaction was ended by cooling to −20° C. The reaction product A.7b was used directly, without further work-up, in stage 3.

Stage 3 (A.7): 2.0 g of the polyurea core A.3 were introduced, were dissolved under nitrogen in 18.0 g of isobutanol, and were admixed with 7.9 g of reaction mixture A.7b. Then the batch was stirred first at 25° C. for 17 hours and subsequently at 80° C. for 6 hours. Following the complete reaction of all the NCO groups (NCO content 0%), the solvent was removed under reduced pressure. Finally this gave the linear-dendritic copolymer A.7 (Mn=5660 g/mol) in the form of a yellow-colored liquid of high viscosity which was fully water-soluble.

Synthesis Example 8

Copolymer Based on a Hydrophobic Hyperbranched Polyurea Core (A.4) and a Linear Peg-b-Polycaprolactone Block Copolymer, Degree of Functionalization 100% (A.8)

Stage 1 (A.8a): 150.0 g of polyethylene glycol monomethyl ether (Mn=500 g/mol) were introduced and were freed from residues of water at 90° C. under reduced pressure. After cooling to room temperature, the batch was placed under nitrogen and admixed with 205.0 g of ε-caprolactone. The mixture was heated to 90° C. and the ring-opening polymerization of the caprolactone was initiated by addition of 355 mg of butyltin tris(2-ethylhexanoate). The batch was heated at 90° C. for a further 18 hours and, after the end of reaction, was cooled to room temperature. The resulting, OH-terminated block copolymer A.8a (Mn=1180 g/mol) was used without further purification directly in stage 2.

Stage 2 (A.8b): 200.0 g of the block copolymer A.8a were introduced, placed under nitrogen, and admixed with 34.1 g of isophorone diisocyanate. The mixture was heated to 50° C. The reaction was initiated by addition of 30 mg of zinc neodecanoate in solution in 1 ml of butyl acetate, and was run over the course of 4 hours at 50° C. to an NCO content of 2.23%. Subsequently the reaction was ended by cooling to −20° C. The reaction product A.8b was used without further work-up directly in stage 3.

Stage 3 (A.8): 18.0 g of the polyurea core A.4 were introduced and dissolved under nitrogen in 72.0 g of isobutanol. The batch was then admixed with 20.0 g of reaction mixture A.8b, and stirred first at 25° C. for 16 hours and subsequently at 80° C. for 4 hours. Following the complete reaction of all the NCO groups (NCO content 0%), the batch was cooled and the solvent was removed under reduced pressure. Finally this gave the linear-dendritic copolymer A.8 (Mn=4020 g/mol) in the form of a yellow-colored liquid of high viscosity which was fully water-soluble.

Solubilization Experiments:

The wavelengths of the UV-spectroscopic measurements (if applicable) are summarized in table 1.

TABLE 1

| Compound to be dissolved | Wavelength of UV measurement [nm] |
|---|---|
| Piroxicam | 356 |
| Carbamazepine | 286 |
| Estradiol | 282 |
| Clotrimazole | HPLC analysis |
| Pyrene | 334 |
| Pyraclostrobin | 277 |
| Fipronil | 280 |

General procedure 1 for solubilization experiments with piroxicam, carbamazepine, estradiol and clotrimazole: Approximately 2 g of polymer were weighed out into a 50 mL glass beaker. Then 0.2 g of each active ingredient was weighed into the batch to give a supersaturated solution. Next, phosphate buffer pH 7.0 was added in an amount such as to give a polymer:phosphate buffer mass ratio of 1:9. The mixture was then stirred at room temperature for 72 hours, using a magnetic stirrer. After a rest time of one hour, unsolubilized active ingredient was removed by filtration. The resulting clear or opaque solution was then analyzed for its active ingredient content by means of UV spectroscopy or HPLC.

TABLE 2

| | Solubility [mg/l] in the presence of | | | |
|---|---|---|---|---|
| | Piroxicam | Carbamazepine | Estradiol | Clotrimazole |
| Without polymer[a] | 420 | 140 | <100 | <100 |
| Polymer A.5 | 11480 | 1550 | 2840 | 2080 |
| Polymer A.6 | 8100 | 1640 | 1650 | 2070 |

[a]not inventive

General procedure 2 for solubilization experiments with pyrene, pyraclostrobin and fipronil: Approximately 100 mg of polymer were weighed out into a 50 mL glass beaker and dissolved in 9.900 g of distilled water. Then 100 mg of each active ingredient was weighed into the batch to give a supersaturated solution. The mixture was then stirred at room temperature for 24 hours, using a magnetic stirrer. After a rest time of one hour, unsolubilized active ingredient was removed by centrifuging. The resulting clear or opaque solution was then analyzed for its active ingredient content by means of UV spectroscopy.

TABLE 3

| | Solubility [mg/l] in the presence of | |
|---|---|---|
| | Pyrene | Fipronil |
| Without polymer[a] | 0.1 | 3 |
| Polymer A.5 | 168 | 456 |
| Polymer A.6 | 149 | 257 |
| Polymer A.7 | 202 | 575 |
| Polymer A.8 | 263 | 767 |

[a]not inventive

Comparison of the solubilizing properties of core, shell, core/shell blends and inventive copolymer The solubility was determined as described in procedure 2.

| | Solubility [mg/l] in the presence of | | |
|---|---|---|---|
| | Pyrene | Fipronil | Water solubility of the polymer |
| Without polymer[a] | 0.1 | 3 | — |
| Polymer A.5 | 168 | 456 | Yes |
| Polymer A.1 (core only)[a] | — | — | No |
| PEG monomethyl ether (shell only)[a] | 3 | 6 | Yes |
| Polymer A.1 + PEG monomethyl ether (mixture of core + shell)[a] | — | — | No (undissolved fractions) |

[a]not inventive

Table 4a shows that the inventive polyurea A.5 (A.1 functionalized with PEG monomethyl ether) has higher solubilizing capacities than the individual constituents, i.e., than the core polymer (A.1), than the shell polymer (PEG monomethyl ether) or than the mixture (i.e., no conalent joining of core polymer and shell polymer.

TABLE 4b

| | Solubility [mg/l] in the presence of | | |
|---|---|---|---|
| | Pyrene | Fipronil | Water solubility of the polymer |
| Without polymer[a] | 0.1 | 3 | — |
| Polymer A.7 | 202 | 575 | Yes |
| Polymer A.3 (core only)[a] | — | — | No |
| Polymer A.7a (shell only)[a] | 171 | 366 | Yes |
| Polymer A.3 + Polymer A.8a (mixture of core + shell)[a] | — | — | No (undissolved mixtures) |

[a]not inventive

Table 4b shows that the inventive polyurea A.7 (A.3 functionalized with A.7a) has higher solubilizing capacities than the individual constituents, i.e., than the core polymer (A.3), the shell polymer (polymer A.7a) or the mixture (i.e., no covalent joining) of core polymer and shell polymer.

The invention claimed is:

1. A composition comprising an amphiphile and an active ingredient having a solubility in water at 20° C. of not more than 2 g/L, wherein the amphiphile comprises a dendritic polyurea which is joined to at least one linear polymer, and wherein the joining is effected by a difunctional linker,
    wherein the difunctional linker is selected from the group consisting of tolylene 2,4-diisocyanate, tolylene 2,6- diisocyanate, 2,4'-diphenylmethane diisocyanate, isophorone diisocyanate, and mixtures thereof, wherein the at least one linear polymer is a block polymer comprising polycaprolactone and polyethylene glycol, wherein the polyethylene glycol is connected to the difunctional linker via the polycaprolactone;

wherein the active ingredient is a pesticide, wherein the molar mass $M_n$ of the at least one linear polymer is greater than 200 g/mol and less than 10,000 g/mol, wherein the dendritic polyurea has a degree of branching per molecule of 10% to 90% and a weight-average molecular weight from 1,000 to 50,000 g/mol, and wherein the at least one linear polymer is a polyethylene glycol monomethyl ether-block-polycaprolactone polymer.

2. The composition according to claim 1, wherein the dendritic polyurea is a hyperbranched polyurea.

3. The composition according to claim 2, wherein the hyperbranched polyurea is obtained by a process comprising the reaction of an at least difunctional blocked di- or polyisocyanate with at least one at least difunctional primary and/or secondary amine, with elimination of the blocking agent.

4. The composition according to claim 3, wherein the blocking agent is a monoalcohol.

5. An amphiphile comprising a dendritic polyurea, wherein the dendritic polyurea is joined to at least one linear polymer, and wherein the joining is effected by a difunctional linker, wherein the difunctional linker is selected from the group consisting of tolylene2,4-diisocyanate, tolylene 2,6-diisocyanate, 2,4'-diphenylmethane diisocyanate, isophorone diisocyanate, and mixtures thereof, wherein the at least one linear polymer is a block copolymer comprising polycaprolactone and polyethylene glycol, wherein the polyethylene glycol is connected to the difunctional linker via the polycaprolactone, wherein the molar mass Mn of the at least one linear polymer is greater than 200 g/mol and less than 10,000 g/mol, wherein the dendritic polyurea has a degree of branching per molecule of 10% to 90% and a weight-average molecular weight from 1,000 to 50,000 g/mol, and wherein the at least one linear polymer is a polyethylene glycol monomethyl ether-block-polvcaprolactone polymer.

6. The amphiphile according to claim 5, wherein the dendritic polyurea is a hyperbranched polyurea.

7. The amphiphile according to claim 6, wherein the hyperbranched polyurea is obtained by a process comprising the reaction of an at least difunctional blocked di- or polyisocyanate with at least one at least difunctional primary and/or secondary amine, with elimination of the blocking agent.

8. The amphiphile according to claim 7, wherein said di- or polyisocyanate used is an oligo- or polyisocyanate having an average molar mass of 300 to 3000 g/mol.

9. The composition of claim 1, wherein the active ingredient has a solubility in water at 20° C. of not more than 0.5 g/L.

10. The composition of claim 1, wherein the difunctional linker is isophorone diisocyanate.

11. The composition of claim 1, wherein the polyethylene glycol of the at least one linear polymer has a molar mass $M_n$ of 300 g/mol to 2000 g/mol.

* * * * *